United States Patent [19]

Tamminen et al.

[11] Patent Number: 5,536,886

[45] Date of Patent: Jul. 16, 1996

[54] PROCESS FOR PREPARING ALKYL ETHERS

[75] Inventors: Esa Tamminen, Espoo; Juhani Aittamaa, Helsinki; Juha Jakkula, Kerava, all of Finland

[73] Assignee: Neste Oy, Espoo, Finland

[21] Appl. No.: 305,920

[22] Filed: Sep. 16, 1994

Related U.S. Application Data

[63] Continuation-in-part of PCTFI93/00098, Mar. 18, 1993.

[30] Foreign Application Priority Data

Mar. 18, 1992 [FI] Finland ................................. 921174

[51] Int. Cl.⁶ ................................................. C07C 41/06
[52] U.S. Cl. .................................................... 568/697
[58] Field of Search ............................................ 568/697

[56] References Cited

U.S. PATENT DOCUMENTS

| | | | |
|---|---|---|---|
| 4,198,530 | 4/1980 | Wentzheimer et al. | 568/697 |
| 4,299,999 | 11/1981 | Mikitenko et al. | 568/697 |
| 4,475,005 | 10/1984 | Paret | 568/697 |
| 4,503,265 | 3/1985 | Schleppinghoff et al. | 568/697 |
| 4,647,703 | 3/1987 | Torck et al. | 568/697 |

FOREIGN PATENT DOCUMENTS

| | | | |
|---|---|---|---|
| 0078422 | 5/1983 | European Pat. Off. | C07C 41/42 |
| 1594158 | 7/1981 | United Kingdom | C07C 41/42 |
| 9319031 | 9/1993 | WIPO | C07C 41/06 |

*Primary Examiner*—José G. Dees
*Assistant Examiner*—Rosalind A. Williams

[57] ABSTRACT

The invention relates to a process for preparing tertiary alkyl ethers. According to the process the feedstock containing hydrocarbons is fed to a catalytic distillation reactor system, in which the isoolefines, in particular the $C_4$ to $C_7$ isoolefines, of the feed are reacted with an alkanol in the presence of a cation exchange resin in order to produce tertiary alkyl ether products. The reaction product containing the ethers is removed from the distillation system as the bottoms product and, if necessary, it is subjected to an additional treatment for producing a gasoline component. The unreacted alkanol is removed as the overhead product of the distillation. According to the invention, the distillate withdrawn mainly contains an azeotrope of $C_4$ hydrocarbons and alkanol, the $C_4$ amount of which at least approximately corresponds to the $C_4$ hydrocarbon concentration of the hydrocarbon feed, a substantial amount of the unreacted alkanol being removed in the form of said azeotrope. By means of the invention the need for a separate alkanol washing unit is eliminated in the apparatus which considerably reduces apparatus investment costs.

14 Claims, 2 Drawing Sheets

PROCESS FOR PREPARING ALKYL ETHERS

This application is a continuation-in-part of PCT international application No. PCT/FI93/00098 which has an international filing date of Mar. 18, 1993 which designated the United States, the entire contents of which are hereby incorporated by reference.

BACKGROUND OF THE INVENTION

1. Field of the Invention

The present invention concerns a process for preparing tertiary alkyl ether products which are used, in particular, as a components of motor fuels. The products contain, for instance t-amyl methyl or t-amyl ethyl ethers and possibly heavier tertiary alkyl ethers. According to the process, the isoolefins, in particular the $C_5$-$C_7$ isoolefins of the feedstock are reacted with a suitable alkanol for preparing the corresponding ethers. These ethers are removed together with the bottoms product of the distillation-reaction system and, if necessary, they are further processed in order to prepare a motor fuel component. Unreacted alkanol is removed with the overhead product of the distillation.

2. Description of Related Art

In order to improve the anti-knocking characteristics of motor fuels without using organolead compounds, and in order to reduce the concentration of detrimental components in the exhaust gases, tertiary alkyl ethers are added to the fuels. The oxygen-containing ether group of these compounds has been found to improve the combustion process in a favourable way as far as the afore-mentioned aspects are concerned. Suitable alkyl tert-alkyl ethers are methyl t-butyl ether (MTBE), ethyl t-butyl ether (ETBE), t-amyl methyl ether (TAME), t-amyl ethyl ether (TAEE) and t-hexyl methyl ether (THME), just to mention a few examples. These ethers are prepared by etherification of a monovalent aliphatic alcohol with an isoolefin. The reaction can be carried out in a fixed bed reactor, in a fluidized bed reactor, in a tubular reactor or in a catalytic distillation column.

In a fixed bed reactor, the feed components are reacted in the presence of a solid catalyst particles, said catalyst particles being contained in a layer which remains unmixed, because the liquid flow rates are so low that the catalyst particles do not separate from each other. They form a so-called fixed bed. On the other hand, in a fluidized bed reactor, the flow rate of the liquid phase is so high that the catalyst particles float separately in the fluidized bed of the reactor.

When the etherification is carried out in a catalytic i.e. reactive distillation process, the catalyst particles can form a fixed or fluidized bed in the column. The particular benefit which can be obtained by the catalytic distillation process is that the reaction and the separation of the products take place in the same vessel.

The etherification reaction is an exothermic equilibrium reaction, and the maximum conversion is determined by the thermodynamic equilibrium of the reaction system. Typically, by carrying out reaction and separation in one and the same reactive distillation column, it is possible to obtain an about 90% conversion in the case of TAME, whereas only a 65 to 70% conversion is obtainable in a fixed bed reactor.

Ion exchange resins can be used as catalysts. Generally the resin used comprises a sulfonated polystyrene/divinyl benzene based cation exchange resin (sulfonated polystyrene cross-linked with divinylbenzene) having particle sizes in the range from 0.1 to 1 mm.

Commercially there are two alternative TAME processes available. The first one comprises fixed bed reactors, columns for product separation distillation and a methanol separation unit. The other alternative differs from the first one in the sense that the product distillation is replaced by a catalytic distillation unit, which substantially improves the TAME conversion.

In a third completely novel process alternative, which is described in our international patent application WO 93/19031 the second alternative mentioned above has been modified by transferring the catalyst from the inside of the distillation column into a separate external reactor which is being fed from the product separation distillation unit. The side reactor product is recycled back to the same product separation distillation unit.

Ethers heavier than TAME can also be produced by all of the above mentioned processes. The process described in our international patent application mentioned above can also be used for preparing other lower alkyl ethers, such as t-amyl ethyl ether (TAEE) and the corresponding heavier ethyl ethers.

The prior an processes are hampered by certain problems. Thus, the overhead product of the product distillation unit of the TAME processes contains large amounts of light hydrocarbons and, for this reason, also so much unreacted methanol that the overhead product cannot be used in an alkylation unit or directly as a gasoline component. The methanol must be removed first which is the reason why a separate methanol separation unit has to be included in the process. The methanol separation generally comprises extraction with water and methanol-water distillation.

Similar problems are encountered with the other alkanols.

SUMMARY OF THE INVENTION

The present invention aims at eliminating the problems associated with the prior art by providing a completely novel process for producing tertiary alkyl ethers.

The invention is based on the concept of operating the product distillation of a catalytic distillation reactor system in such a way that most and preferably practically all the alkanol which is removed with the distillate is bound to the hydrocarbons of the distillate forming an azeotrope with them.

It is known per se that, e.g., methanol forms an azeotrope with the components present in etherification mixtures of tertiary alkyl ethers. There are several applications known, wherein the unreacted methanol is removed from the top of the distillation column together with $C_4$ hydrocarbons. Prior art processes of this kind are described in, e.g, the Published German Patent Application No. 2,705,538, the Published European Patent Application No. 78,422, U.S. Pat. No. 4,198,530 and the Swedish Applications Laid Open Nos. 448,452 and 459,175.

The above-mentioned prior art publications concern the preparation of pure ether products. The present invention aims at producing ether products which as such can be used as gasoline components and which, except for the $C_4$ hydrocarbons, also contain at least some of the inert hydrocarbon components of the feedstock. Thus, according to the present invention, the unreacted hydrocarbons are mainly removed with the bottoms product of the distillation. The overhead product withdrawn from distillation substantially contains an azeotrope formed by the $C_4$ hydrocarbons and the alkanol used. The amount of $C_4$ hydrocarbons in the distillate corresponds at least approximately to the amount of $C_4$ hydrocarbons present in the feed. In this way, an essential part of the unreacted alkanol is removed in the form of said azeotrope.

DETAILED DESCRIPTION OF THE INVENTION

Figure 1:
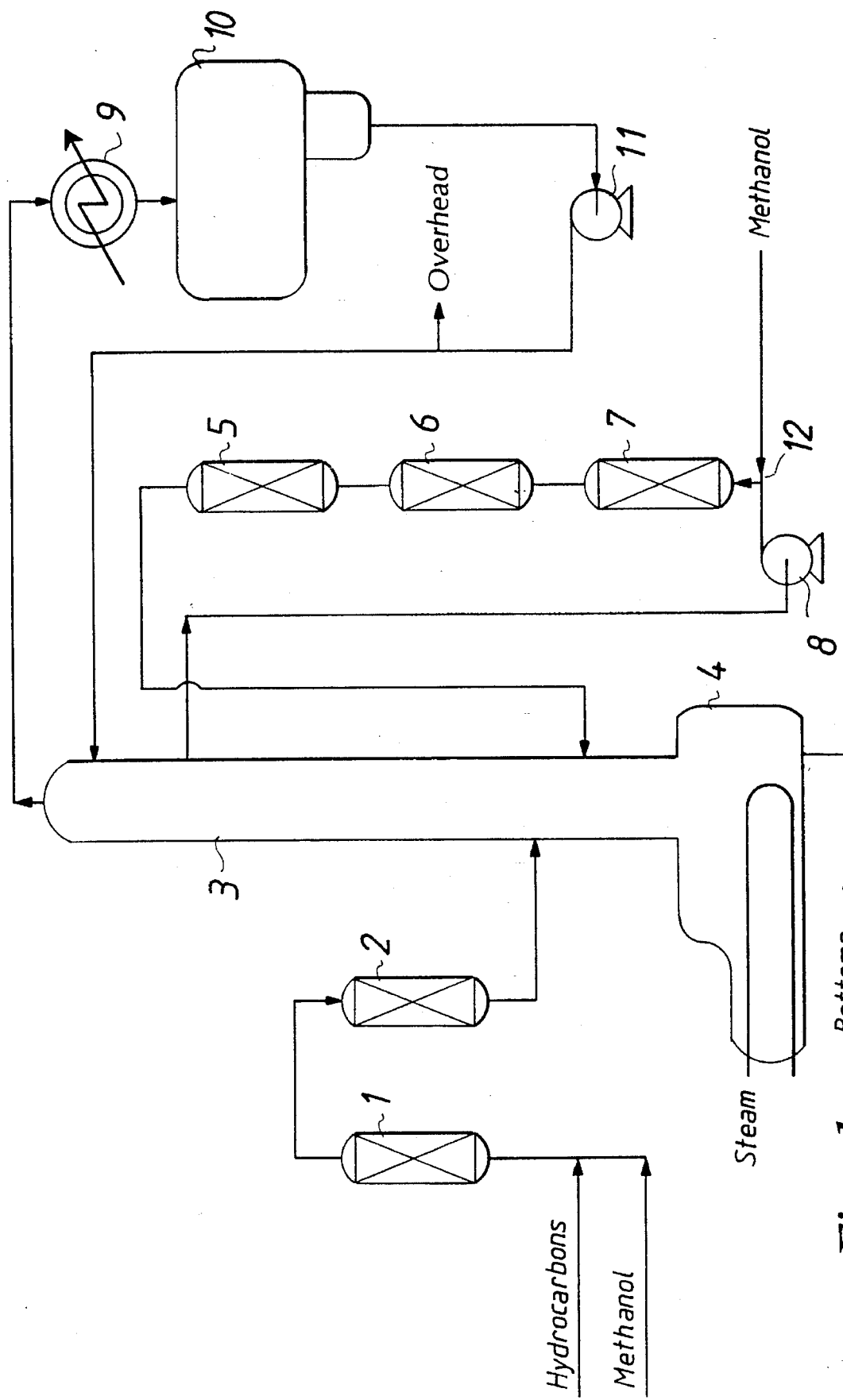
FIG. 1 depicts a simplified scheme of the TAME process.

Within the scope of this application, the expression "catalytic distillation reactor system" denotes an apparatus, wherein the ether product reaction and the separation of the products takes place at least partially simultaneously. The apparatus may comprise a conventional reactive distillation column or a distillation column combined with at least one side reactor.

The term "alkanol" includes lower alkyl alcohols capable of forming azeotropes with the saturated and unsaturated hydrocarbons, in particular the $C_3$-...$C_7$-hydrocarbons, of the hydrocarbon feedstock. As specific examples of the alkanols, the following can be mentioned: methanol, ethanol, n-propanol, i-propanol, n-butanol, i-butanol and t-butanol, methanol and ethanol being particularly preferred.

The process according to the present invention comprises an etherification process wherein a feedstock containing hydrocarbons, in particular $C_{4-7}$ hydrocarbons, is fed into a catalytic distillation reactor system. The $C_{5-7}$ isoolefines of the feedstock are reacted with an alkanol in the presence of a cation exchange resin to form tertiary alkyl ethers.

According to the invention, any catalyst typically used in etherification processes can be employed. Preferably conventional cation exchange resins are used. However also different kinds of zeolites are also possible. Thus, the resin may contain sulfonic acid groups and it can be obtained by polymerization or copolymerization of aromatic vinyl compounds followed by sulfonation. Examples of aromatic vinyl compounds suitable for preparing polymers of copolymers are: styrene, vinyl toluene, vinyl naphthalene, vinyl ethylbenzene, methyl styrene, vinyl chlorobenzene and vinyl xylene. The acid cation exchange resin typically contain some 1.3 to 1.9 sulfonic acid groups per aromatic nucleus. Preferred resins are based on copolymers of aromatic monovinyl compounds with aromatic polyvinyl compounds, particularly, divinyl compounds, in which the polyvinyl benzene content is from about 1 to 20 wt-% of the copolymer. The ion exchange resin preferably has a granular size of about 0.15 to 1 mm. In addition to the above resins perfluorosulfonic acid resins, which are copolymers of sulfonyl fluorovinyl ethyl and fluorocarbon, can be used.

The alkyl ethers are removed from the distillation reactor system with the bottom product and, if desired, subjected to further processing in order to produce a gasoline component. As mentioned above, substantially all of the unreacted hydrocarbons are also removed with the bottoms product of the distillation.

According to the present invention the distillation column of the reactive distillation unit is operated in such a way that the alkanol is heavier than the hydrocarbons at the top of the distillation column. Therefore, the alkanol not bound to the hydrocarbons in the form of an azeotrope will tend to flow downwards within the column. At the same time the vapor-liquid-equilibrium between $C_5$ and heavier hydrocarbons and the alkanol at the bottom of the column is maintained at such a value that the alkanol is lighter than the hydrocarbons. This causes the alkanol to flow upwards from the bottom of the column. Thus, the alkanol will circulate within the distillation system between the top and the bottom of the column. By fitting a reaction bed in the distillation column or by conducting a side stream from the column through a reaction bed in a side reactor, an alkanol consuming reaction can be created which will remove the alkanol from the system.

The alkanols, in particular methanol and ethanol, form azeotropes with the hydrocarbons of the feedstock. The heavier the hydrocarbons, the greater the alkanol concentration of the hydrocarbon-alkanol-azeotrope. According to the present invention, in order to minimize the amount of unreacted alkanol removed from the distillation process, substantially only the $C_4$-hydrocarbon-alkanol azeotropes are taken as an overhead product. These azeotropes are the lightest hydrocarbon-alkanol azeotropes and have the smallest alkanol concentrations.

Thus, according to the present invention, the amount of unreacted alkanol can be controlled by adjusting the amount of $C_4$ hydrocarbons in the feed so that it correlates with the amount of alkanol. The less there are $C_4$ hydrocarbons in the feed, the less distillate can be removed and the less alkanol is removed from the process. By increasing the amount of $C_4$ hydrocarbons in the feed the distillate flow rate can be increased without any change of the relative amount of free unreacted alkanol in the overhead product. Therefore, if desired, $C_4$ hydrocarbons (or even $C_3$ hydrocarbons) can deliberately be added to the process so that the intended effect is achieved.

When operating the process according to the invention, the alkanol concentration of the bottoms product of the column can easily be reduced to as small a value as desired. In the case of methanol, it is possible to reduce its concentration in the bottoms product to below 100 ppm. The amount of alkanol in the distillate will correspond to the amount bound by the azeotrope, only. The composition of the azeotrope and, thus, the amount of removed alkanol depends on the hydrocarbon composition of the overhead product and the operating pressure of the distillation. To mention an example based on the production of TAME: if $C_4$ hydrocarbons make up the main part (over 90% ) of the overhead product, there will remain some 0.1 to 5.0% by weight of methanol depending on the distillation pressure and the amount of $C_5$ hydrocarbons. The more $C_5$ hydrocarbons are included in the overhead product, the more methanol will be removed with it (there may be less than 90% by weight of the $C_4$ hydrocarbons in the overhead product).

According to a preferred embodiment of the present invention, the reactive distillation system comprises a distillation column which is in fluid contact with at least one side reactor containing a catalytic reaction bed. The side stream flow can be effected as a forced circulation by using a pump or by thermosiphon. This process alternative is described in more detail in our copending patent application WO 93/19031 which relates to a process and an apparatus for preparing tertiary ethers.

According to a preferred embodiment the location of the drawoff from the column to the side reactor is selected in such a way that the vapour-liquid equilibrium ratio (the K-value) of the alkanol is smaller than 1 on the (theoretical) trays above it. If TAME is prepared, the process can be operated in such a way that the K-value of the methanol is smaller than 1 already on the tray immediately above the drawoff tray. In the TAEE process, there is (are) usually 1 or 2 (theoretical) tray(s) between the drawoff tray and the first tray above it which has a K-value for ethanol smaller than 1. The reaction product containing the alkanol is returned from the side reactor to the column and it is fed to a tray having an alkanol K-value greater than 1. As a result the alkanol gets more enriched in the vapor phase than do the hydrocarbons. The side stream makes up 40 to 90%, typically about from 60 to about 70% of the total liquid flow within the column. The use of a side reactor is preferred, e.g., for the reason that the conditions prevailing in the distillation column can be influenced by changing the drawoff location of the side stream and by feeding more alkanol to the reaction bed.

The invention can also be applied to a conventional catalytic distillation reactor. It is operated in the same way as a side reactor process. The only difference is that the alkanol consuming reaction takes place within the column.

The invention is preferably carried out in connection with the TAME and the TAEE processes.

In connection with the TAME process, the overhead product obtained can be forwarded to a MTBE unit. Since it contains some impurities ($C_5$ hydrocarbons, as far as the MTBE process is concerned), the overhead product can be introduced either in the feed of the MTBE unit, which means that the $C_5$ hydrocarbons remain in the MTBE product, or to the methanol washing unit of the MTBE unit. In the latter case the $C_5$ hydrocarbons end up in the raffinate stream of the MTBE unit (which contains mainly $C_4$ hydrocarbons).

Alternatively, the overhead product of the distillation can—because it contains only minute amounts of methanol and because the overhead is very small compared to the feed—also be combined with the bottoms product of the distillation in order to form a gasoline component. If necessary, the mixture is subjected to an additional treatment. According to a preferred embodiment of the invention, the $C_4$ hydrocarbon content of the feed is, however, deliberately kept so small that the mixture of the overhead and the bottoms products can be used as such as a component of motor fuels.

Considerable benefits are achieved by means of the invention. Thus, due to the disclosed arrangement all of the unreacted alkanol, which comes out from the distillation column, is bound to an azeotrope. Since the amount of the removed alkanol is small, no separate alkanol washing unit is longer needed. This considerably diminishes the investment cost of the apparatus.

In the following the invention will be described in more detail with reference to FIG. 1 which depicts a simplified scheme of the TAME process described in working example 1.

In the test arrangement according to the example, the hydrocarbon feedstock and the methanol are mixed together, the mixture is heated and fed through the prereactor part 1, 2. The hydrocarbon feedstock may, for instance, be a hydrocarbon fraction containing isoolefins, such as a hydrocarbon cut of a cat cracker, containing a mixture of isoolefins. The prereactors consist of two reactors filled with ion exchange resin beds. The reactors can be fixed or fluidized bed or tubular reactors. The reactors may be arranged in series, as shown in the figure, or in parallel. If there are more than two prereactors they may also be arranged in series/parallel. Because of the reaction there is a temperature rise in the prereactors in the range from about 5° to about 15° C. depending on the efficiency of the reactor insulation. From the prereactors the mixture is conducted to distillation column 3. At the bottom of the distillation column there is a steam reboiler 4. The distillation column can be a packed column or one provided with valve, sieve or bubble-cap trays. The overhead of the column is removed via a condenser 9 to a reflux drum 10, from which the overhead is removed by means of a pump 11. A part of the overhead,is forwarded to further processing, for instance to a MTBE process, and a part thereof is returned to the column. TAME and heavier ethers are removed with the bottoms product. In addition to the ethers, the bottoms product also contains unreacted $C_{5+}$ hydrocarbons. The reflux ratio of the column is preferably from about ½ to 200. Even greater ratios can be used in pilot plant equipments. According to the invention, the reflux ratio is adjusted so that the distillate amount removed from the process at least substantially corresponds to the amount of $C_4$ hydrocarbons of the feed.

Next to the distillation column 3 a side reactor system has been arranged, which consists of three reactors 5, 6, 7 in series. The reactors can, if desired, be replaced by one larger reactor. According to the mode of circulation the reactors can be fixed or fluidized bed reactors or tubular reactors, as mentioned above in the general part of the description. The side reactors are fed with a liquid stream taken from the column. The pressure of the liquid stream is increased by pump 8. The side stream is preferably taken from a tray which is located below trays having methanol K-values less than 1. Additional methanol can, if needed, be fed to the side reactor feed before the side reactor (point 12). The reactor feed can be cooled to the reaction temperature before the side reactor. Due to heat losses the temperature rises only by a few degrees in the side reactors. From the side reactor system 5 to 7 the liquid flow is routed back to column 3. It is then returned to a plate having a K-value greater than 1.

According to the example, the reactor effluent enters the column at a location below the feed coming from the prereactors 1, 2. The aim of this arrangement is to make the column 3 operate in such a manner that the methanol in the overhead product is bound to the $C_4$ hydrocarbons in the form of an azeotrope.

Figure 2:
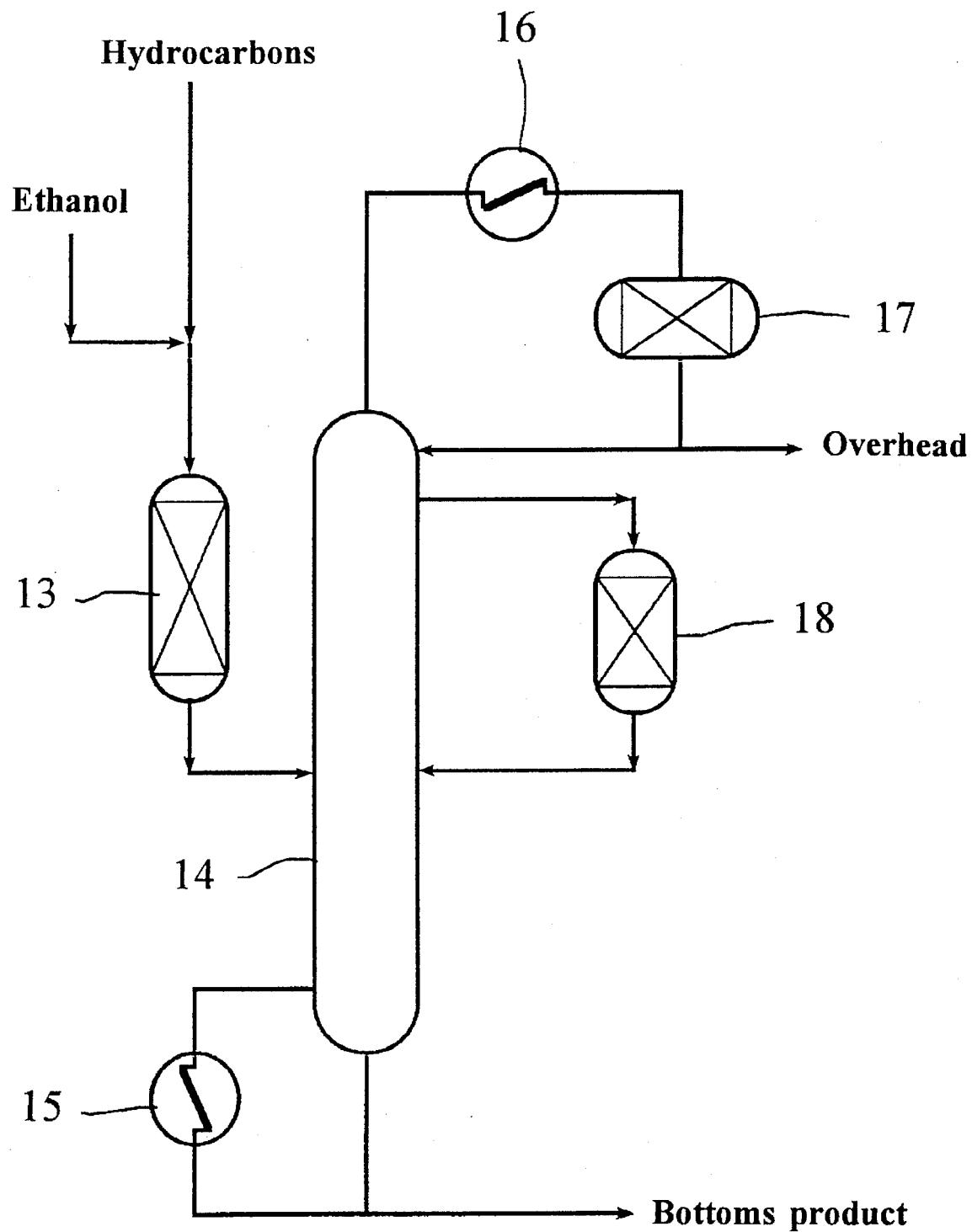
FIG. 2 depicts a simplified scheme of the TAEE process.

Other alkanol ethers can be prepared in a similar manner. FIG. 2 shows the simplified process scheme of the TAEE process of working example 2. The process configuration, the process equipment and the operation conditions are basically the same as in the above example. Thus, the hydrocarbon feedstock and the ethanol are mixed together and the mixture is through a prereactor 13 filled with ion exchange resin beds. From the prereactor 13 the mixture is conducted to distillation column 14. At the bottom of the distillation column there is a steam reboiler 15. The distillation column 14 can be a packed column or one provided with valve, sieve or bubble-cap trays. The overhead of the column is removed via a condenser 16 to a reflux drum 17. A part of the overhead is forwarded to further processing, for instance to a ETBE process, and a part thereof is returned to the column. TAEE and heavier ethers are removed with the bottoms product. In addition to the ethers, the bottoms product also contains unreacted $C_{5+}$ hydrocarbons. The reflux ratio of the distillation process is adjusted so that the distillate amount removed from the process at least substantially corresponds to the amount of $C_4$ hydrocarbons of the feed.

Next to the distillation column 14 a side reactor 18 has been arranged. The side reactor is fed with a liquid stream taken from the column. The side stream is preferably taken from a tray which is located below trays having ethanol K-values less than 1. However, the hydrocarbon-ethanol-balance in the column will usually settle around the side drawoff in such a way that there are one or two theoretical trays above the draw off tray on which the K-value of ethanol is still greater than 1. However, on the following trays above, the K-value will be less than 1.

Additional ethanol can, if needed, be fed to the side reactor feed before the side reactor. From the side reactor 18 the liquid flow is routed back to column 14 to a plate having a K-value greater than 1.

The following working examples will clarify the invention:

EXAMPLE 1

Preparation of TAME by using a catalytic distillation reactor system with prereactors and side reactors The apparatus configuration depicted in FIG. 1 was used. The inner diameter of the prereactors 1 and 2 was 102.3 mm and their lengths were 1500 mm. They were filled with the catalyst Dowex® M-32 supplied by Dow Chemicals Inc. The catalyst comprises an acid sulfonated polystyrene/divinyl benzene based cation exchange resin. The inner diameter of the distillation column 3 was 160 mm, its height was 11,000 mm and it was equipped with packings. There were 6 beds of packings. The three side reactors 5 to 7 were arranged in series and each of them had an inner diameter of 154.1 mm, and a height of 1,150 mm. These reactors were also filled with the catalyst Dowex® M-32.

The hydrocarbon feed rate was 30 kg/h. Its composition is shown in Table 1. The table also indicates the amounts of methanol feed. The methanol and the hydrocarbon feed were mixed together and heated to 58° C. Then the mixture was conducted through prereactors 1 and 2, which caused the temperature to increase by 9° C. From the prereactors the mixture was conducted to the distillation column 3, the feed point being situated between the third and the fourth packed bed. The temperature of the distillation column was 40° C. at the top and 95° C. at the bottom, the operating pressure being 400 kPa.

A sidestream was withdrawn from the column at a point between the second and the third packed beds. The temperature of said sidestream was 70° C. It was cooled to 60° C. and fed to the side reactors 5 to 7. The liquid feed rate was 60 kg/h. The pressure of the feed was increased by pump 8 and methanol was added, as indicated in Table 1. The temperature rose by 3° C. in the side reactors (the temperature rise depended to some extent on the heat losses). From the side reactors the flow was routed back to the column, the feedback point of the side reactor being between the fourth and the fifth packing bed.

At the top of the column distillate was withdrawn, the composition of which is indicated in Table 1. The composition of the bottoms product is also shown in Table 1. The K-values of the components within the column are depicted in Table 3.

Three tests were carried out, no methanol being added to the side reactors in the first two tests. The methanol addition increases the yield of TAME, but it may also increase the amounts of unreacted methanol removed with the overhead product. In the exemplified case, at a reflux ratio of 110, said three tests produced overhead products containing 94.03, 95.32 and 60.51% by weight, respectively, of $C_4$ hydrocarbons. The feed contained 2.4% by weight of $C_4$ hydrocarbons, i.e. about 0.7 kg.

As the data indicated below will show, the first two tests in which approximately as much distillate was taken (0.73 kg) from the column as there were $C_4$ hydrocarbons in the feed, rather low methanol concentrations were obtained. In the third test the distillate amount was almost twice as large as the amount $C_4$ hydrocarbons of the feed. As a result, there was almost 4% methanol in the overhead product, i.e. almost twice as much as in the first test.

TABLE 1

| | | Test results of TAME preparation | | | | | |
|---|---|---|---|---|---|---|---|
| | | Test 1 | | Test 2 | | Test 3 | |
| Methanol feed (kg/h); | | | | | | | |
| to the prereactor | | 2.4 | | 2.6 | | 2.6 | |
| to the side reactor | | 0 | | 0 | | 0.5 | |
| Component (% by weight) | Feed | Bottom | Dist. | Bottom | Dist. | Bottom | Dist. |
| $C_4$ hydrocarbons | 2.41 | 0.34 | 94.03 | 0.01 | 95.32 | 0.01 | 60.51 |
| 2-Me-1-butene | 7.50 | 0.34 | | 0.31 | | 0.13 | |
| 2-Me-2-butene | 13.74 | 6.51 | | 5.89 | | 2.51 | |
| Remaining $C_5$ | 47.91 | 45.25 | 2.56 | 44.96 | 1.91 | 44.30 | 35.08 |
| Reacting $C_6$ | 6.91 | 4.94 | | 4.89 | | 4.71 | |
| Remain. $C_{6+}$ | 21.53 | 20.36 | | 20.23 | | 20.50 | |
| Methanol | | 0.04 | 2.99 | 0 | 2.24 | 0.53 | 3.80 |
| TAME | | 20.17 | | 21.36 | | 24.51 | |
| THME | | 2.21 | | 2.21 | | 2.59 | |
| TAOH | | 0.16 | | 0.14 | | 0.20 | |
| DME | | | 0.42 | | 0.53 | | 0.61 |
| Total | 100 | 100 | 100 | 100 | 100 | 100 | 100 |
| Amount (kg/h) | 29 | 30.7 | 0.73 | 30.9 | 0.73 | 30.9 | 1.15 |

TAME = tert-amyl methyl ether
THME = tert-hexyl methyl ether
TAOH = tert-amyl alcohol
DME = dimethyl ether The typical methanol concentrations in the column are as follows:

TABLE 2

Methanol concentrations of the TAME column

|  | Dist. | Between the 1st and 2nd beds | Drawoff |
|---|---|---|---|
| MeOH [wt.-%] | 2.24 | 10.2 | 2.24 |

TABLE 3

K-values in the TAME column

| Tray Component | Side draw Liquid wt-% | Side draw K-value | Tray above side draw Liquid wt-% | Tray above side draw K-value | Feed Liquid wt-% | Feed K-value | Side draw feedback Liquid wt-% | Side draw feedback K-value |
|---|---|---|---|---|---|---|---|---|
| DME | 0 | 5.3 | 0 | 4.48 | 0 | 6.76 | 0 | 6.60 |
| $C_4$ | 9.54 | 1.15 | 10.69 | 1.12 | 3.66 | 2.24 | 8.43 | 2.12 |
| MeOH | 2.24 | 1.51 | 2.34 | 0.96 | 0.18 | 4.99 | 0.12 | 4.64 |
| $C_5$ | 79.54 | 0.92 | 78.54 | 0.9 | 58.1 | 1.21 | 70.48 | 1.13 |
| 2M1B | 0.61 | 0.88 | 0.55 | 0.85 | 0.42 | 1.17 | 0.25 | 1.10 |
| 2M2B | 4.55 | 0.71 | 4.39 | 0.73 | 5.62 | 0.96 | 4.06 | 0.89 |
| TAME | 0 | 0.19 | 0 | 0.17 | 4.15 | 0.33 | 3.66 | 0.30 |
| TAOH | 0.05 | 0.23 | 0 | 0.21 | 0.09 | 0.88 | 0.10 | 0.82 |
| 2M2P | 0.04 | 0.31 | 0 | 0.31 | 4.76 | 0.45 | 2.54 | 0.41 |
| THME | 0 | 0.07 | 0 | 0.06 | 1.05 | 0.14 | 0.67 | 0.13 |

2M1B = 2-methyl-1-butene
2M2B = 2-methyl-2-butene
2M2P = 2-methyl-2-pentene

Table 3 shows that the K-values of methanol increase rapidly from the top of the column towards its bottom, from the side draw towards the hydrocarbon feed, cf. the figure. Thus, by restricting the amount of distillate removed in accordance with the invention, it is possible to achieve the conditions described above in the general part of the description in which methanol flows downwards from the top of the column, revapourizing at the bottom of the column. Since, at the feedback point, the K-value of the methanol coming from the side reactor is greater than 1, side reactor circulation will enrich the vapor with methanol which enhances the methanol circulation.

EXAMPLE 2

Preparation of TAEE by using a catalytic distillation reactor system with a prereactor and a side reactor The apparatus configuration depicted in FIG. 2 is used. The main column contains 60 theoretical trays, the reflux ratio is 150 and the operational pressure 589 kPa. The temperature at the top of the column is 68.6° C. and at the bottom 101.9° C. The prereactor and the side reactor are both operated at an isothermal temperature of 50° C.

The hydrocarbon feedstock (33.000 kg/h) comprises FCC light gasoline having the following composition:

| $C_4$ | 0.6 wt-% |
|---|---|
| 2M1B | 8.5 wt-% |
| 2M2B | 17.7 wt-% |
| $C_5$ remain. | 72.5 wt-% |
| $C_6$ react. | 0.0 wt-% |
| $C_{6+}$ remain. | 0.8 wt-% |
| Total | 100.0 wt-% |

The feedstock contains no ethanol or TAEE. All of the ethanol used for the etherification reaction is fed into the prereactor. The ethanol feed amounts to 4,200 kg/h.

Table 4 indicates the products of the TAEE preparation process.

TABLE 4

Products of the TAEE process

|  | Distillation Column | |
|---|---|---|
|  | Distillate wt-% | Bottoms product wt-% |
| $C_4$ | 48.71 | 0.00 |
| 2M1B | 0.05 | 0.28 |
| 2M2B | 0.00 | 5.62 |
| Rest of the $C_5$ hydrocarbons | 45.40 | 64.33 |
| Reacting $C_6$ hydrocarbons | 0.00 | 0.00 |
| Rest of the $C_{6+}$ hydrocarbons | 0.00 | 0.75 |
| Ethanol | 5.83 | 0.00 |

TABLE 4-continued

| | Products of the TAEE process | |
|---|---|---|
| | Distillation Column | |
| | Distillate wt-% | Bottoms product wt-% |
| TAEE | 0.00 | 29.03 |
| Total Amount, kg/h | 100.00 376 | 100.00 36,814 |

What is claimed is:

1. Process for preparing an ether product used as a component of motor fuels, said process comprising the steps of feeding a feedstock containing $C_{4-7}$ hydrocarbons, to a catalytic distillation reactor system, reacting the $C_{5-7}$ isoolefins of the feedstock with an alkanol in the presence of a catalyst to form tertiary alkyl ethers, removing the alkyl ethers from the distillation reactor system and substantially all of the unreacted hydrocarbons with the bottoms product of the distillation, and withdrawing an overhead product, which mainly contains an azeotrope of $C_4$ hydrocarbons and the alkanol, the $C_4$ amount of the withdrawn overhead product corresponding at least essentially to the amount of $C_4$ hydrocarbons in the feedstock, whereby an essential part of the unreacted alkanol is removed in the form of said azeotrope.

2. The process according to claim 1, wherein the alkanol comprises methanol or ethanol.

3. The process according to claim 1, wherein the amount of distillate withdrawn from the distillation corresponds at least approximately to the amount of $C_4$ hydrocarbons present in the feed.

4. The process according to claim 1, wherein the distillation of the reaction is carried out in such a way that, at the top of the distillation column, the vapor-liquid equilibrium of the hydrocarbons and the alkanol is such that alkanol is heavier than the hydrocarbons and, at the bottom of the distillation column, the equilibrium of the $C_5$ and heavier hydrocarbons and the methanol at the bottom of the column being such that alkanol is lighter than the hydrocarbons.

5. The process according to claim 1, wherein the amount of unreacted alkanol removed from the process is controlled by adjusting the concentration of $C_4$ hydrocarbons in the feed.

6. The process according to claim 1, wherein the catalytic etherification reaction is carried out in a reactor or reactor system external to the distillation column by circulating a sidestream taken from the column through the reactor and returning it to a tray below the one from which it was taken.

7. The process according to claim 6, wherein the K-value of the alkanol is adjusted to less than 1 on the trays above the drawoff tray.

8. The process according to claim 6, wherein the sidestream is returned to the column at a point where the K-value of the alkanol is greater than 1.

9. The process according to any one of the previous claims, wherein the distillate of the distillation is combined with the bottom product of the distillation in order to produce a mixture, and subjecting, if needed, said mixture to further processing to produce a motor fuel component.

10. The process according to any one of claims 1 to 8, wherein the overhead product of the distillation is combined with the feed of a MTBE production process or with the methanol separation unit thereof.

11. The process according to any one of claim 1 to 8, wherein the overhead product of the distillation is combined with the feed of a ETBE production process or with the ethanol separation unit thereof.

12. The process according to claim 1, wherein the $C_4$ hydrocarbon concentration of the feed is intentionally kept so small that the mixture formed by the distillate and the bottoms product can be used as such as a component of motor fuel.

13. The process according to claim 1, wherein the alkyl ethers are subjected to further processing in order to form a gasoline component.

14. The process according to claim 1, wherein the catalyst comprises an acid cation exchange resin.

* * * * *